United States Patent [19]

Baerts

[11] Patent Number: 5,187,991
[45] Date of Patent: Feb. 23, 1993

[54] DEVICE FOR WITHDRAWING SAMPLES FROM MOLTEN METALS

[75] Inventor: Christiaan E. E. Baerts, Beringen-Paal, Belgium

[73] Assignee: Electro-Nite International N.V., Antwerp, Belgium

[21] Appl. No.: 569,055

[22] Filed: Aug. 17, 1990

[30] Foreign Application Priority Data

Sep. 12, 1989 [DE] Fed. Rep. of Germany ... 8910869[U]

[51] Int. Cl.⁵ ............................................. G01N 1/14
[52] U.S. Cl. .................... 73/864.56; 73/864.58
[58] Field of Search ..................... 73/864.53–864.59, 73/DIG. 9

[56] References Cited

U.S. PATENT DOCUMENTS

| | | | |
|---|---|---|---|
| 3,415,124 | 12/1968 | Collins | 73/864.56 |
| 3,457,790 | 7/1969 | Hackett | 73/864.56 |
| 3,633,890 | 1/1972 | Kozmin | 432/248 |
| 3,646,816 | 3/1972 | Hance et al. | 73/864.56 |
| 3,923,526 | 12/1975 | Takashima | 106/38.22 |
| 3,962,492 | 6/1976 | Phelps | 106/38.27 X |
| 4,120,204 | 10/1978 | Cure | 73/864.57 |
| 4,199,641 | 4/1980 | Aono et al. | 264/300 X |
| 4,326,426 | 4/1982 | Falk | 73/864.59 |
| 4,838,336 | 6/1989 | Gray | 73/864.6 X |
| 4,848,438 | 7/1989 | Gray | 73/864.56 X |
| 5,060,530 | 10/1991 | Haughton | 73/864.53 |

FOREIGN PATENT DOCUMENTS

| | | | |
|---|---|---|---|
| 0087219 | 8/1983 | European Pat. Off. | |
| 2510446 | 9/1977 | Fed. Rep. of Germany | |
| 3418320 | 11/1984 | Fed. Rep. of Germany | |
| 2218022 | 9/1974 | France | 73/864.56 |
| 2546625 | 11/1984 | France | |
| 2560993 | 9/1985 | France | |
| 2013852 | 8/1979 | United Kingdom | 73/864.59 |

*Primary Examiner*—Tom Noland
*Attorney, Agent, or Firm*—Panitch, Schwarze, Jacobs & Nadel

[57] ABSTRACT

Two metallic half dishes are fitted together to form a sample container arranged in the hollow space of a carrying tube. The sample container serves to withdraw samples from molten metals. The hollow space surrounding the sample container is filled with granules made of a refractory material, such as corundum. The hollow space is preferably bordered on its sides by a cardboard tube, which is inserted into the carrying tube.

3 Claims, 1 Drawing Sheet

DEVICE FOR WITHDRAWING SAMPLES FROM MOLTEN METALS

FIELD OF THE INVENTION

The invention concerns a device for withdrawing samples from molten metals, comprising a sample container or vessel formed from two metallic half dishes. The dishes fit together to form a shallow sampling chamber and are arranged in the hollow space of a carrying tube. The sample container is provided with a neck-shaped inlet orifice for the melt, and an externally projecting small quartz pipe fits into the orifice.

BACKGROUND OF THE INVENTION

When such devices known in the art are immersed in molten metal, depending upon the immersion depth, considerable pressures occur within the sampling chamber due to the high density of the molten metal, which for steel is equal to 7.8 kg/dm$^3$. These pressures can cause the half dishes to spread apart; that is, the sampling chamber opens, so that molten metal can flow out. This leads to unwanted edge formations (burrs) on the solidified sample. In order to avoid this problem, it is known to hold the two half dishes together with a strong spring clip, a clamp, or by some similar means, as shown, for example, in German Offenlegungschrift 34 18 320.

Another problem concerns supporting and fixing the sample container in the hollow space of the carrying tube. German Patent No. 25 10 446 provides that the sample container be situated in a preformed carrier made, for example, of a ceramic material, which fixes the sample container in place and at the same time holds the two half dishes together.

It is also known to embed the two half dishes in a molded body in the hollow space of the carrying tube, the molded body being made of resin-agglomerated sand. Using a sand of this type has the disadvantage that, while the molten metal is flowing into the sampling chamber, the resin burns and the resultant gases and vapors can penetrate into the sampling chamber. This can result in adulteration of the chemical composition of the sample. In addition, there exists the danger that, as a result of the gases in the sampling chamber, a counter-pressure builds up, which prevents the metal from flowing in.

SUMMARY OF THE INVENTION

The purpose which lies at the heart of the present invention is to create as simply as possible a support for the sample container in the hollow space of the carrying tube of known disposable devices for withdrawing samples. At the same time avoiding the disadvantages that occur when resin-agglomerated sand is used, it is possible to prevent the two half dishes from opening due to the ferrostatic pressure occurring during immersion in the melt.

To achieve this purpose, the invention, which proceeds from a device of the type described at the outset, provides that the hollow space surrounding the sample container is filled with granules made of a refractory material. According to the invention, the particle size of the granular material, which is preferably made of corundum, is greater than 100 μm.

One embodiment of the invention provides that the granules surrounding the sample container are bound with a refractory, inorganic binding material and that the hollow space is bordered on its sides by the carrying tube.

An additional embodiment of the invention provides that the hollow space is bordered on its sides by a cardboard tube inserted in the carrying tube and, on the end opposite the inlet end, by a layer of porous, refractory material, over which a perforated cover plate is arranged. The invention also provides that the small quartz pipe projecting externally from the face of the immersion end of the device is surrounded by a metal pipe.

According to the invention, the neck-shaped inlet orifice of the sample container is held in the central borehole of a head piece, which is inserted in the front end of the carrying tube. Fixing the small quartz pipe in the area of the expanded end of the borehole of the headpiece is preferably accomplished by means of a packing material made of refractory cement. In addition, the immersion end of the metal pipe can be covered with a slag cap, and an oxidation agent ca be arranged in the front end of the small quartz pipe.

BRIEF DESCRIPTION OF THE DRAWINGS

The foregoing summary, as well as the following detailed description of presently preferred embodiments of the invention, will be better understood when read in conjunction with the appended schematic drawings. It is understood, however, that this invention is not limited to the precise arrangements illustrated.

DETAILED DESCRIPTION OF PREFERRED EMBODIMENTS

Figure 1:
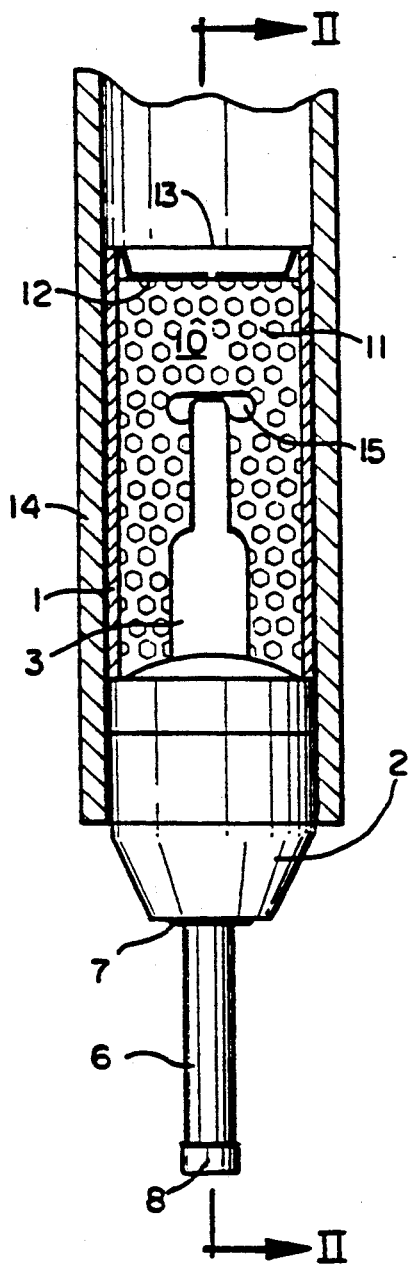
FIG. 1 is a partial cross-sectional side view of the lower end of a device for withdrawing samples from molten metals.
Figure 2:
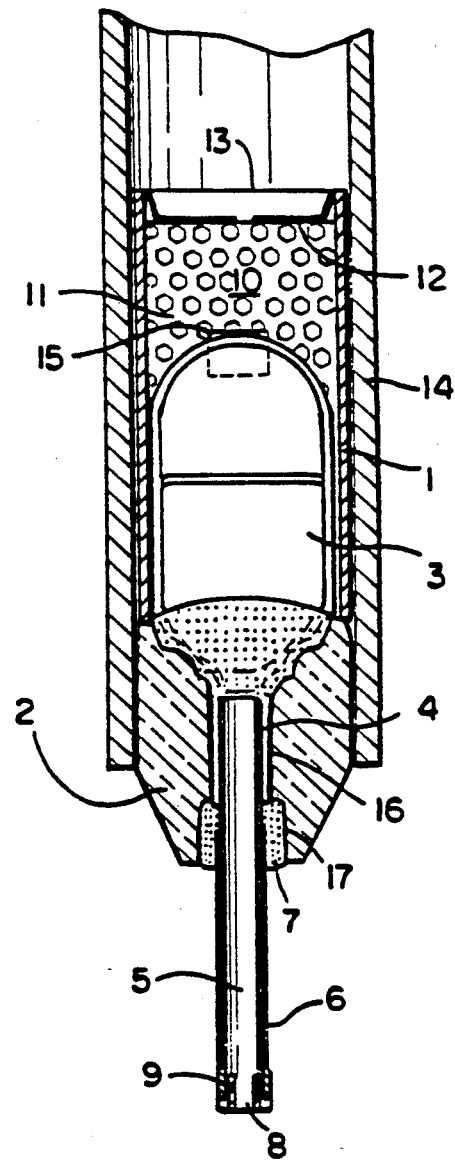
FIG. 2 is a cross-section view along line II—II of FIG. 1.

A cardboard tube 1 is arranged in the lower end of a carrying tube 14 in whose immersion end a headpiece 2 made of refractory material is inserted. This headpiece 2 encloses the cardboard tube 1 and is provided with a central borehole 16. The sample container 3 formed from two metallic half dishes is provided with a neck-shaped inlet orifice 4, into which a small quartz pipe 5 is inserted that projects from the face of the lower end of the headpiece 2. Outside of the inlet orifice 4, a metal pipe 6 is placed over the small quartz pipe 5. Fixing the two pipes in the area of an expanded end section 17 of the borehole 16 on the front (in the drawing, lower) end of the headpiece 2 is accomplished by means of a packing material 7 made of refractory cement. The front end of the metal pipe 6 is equipped with a slag cap 8. In addition, an oxidation agent 9 can be inserted in the front end of the small quartz pipe 5.

According to the invention, the hollow space 10 formed by the cardboard tube 1 is filled with granules 11 made of a refractory material, in particular of corundum ($Al_2O_3$). The surface of the filling opposite the immersion end is covered on the upper end of the cardboard tube with a layer 12 made of a porous, refractory material, over which a perforated cover plate 13 is arranged. To facilitate assembly, a spring clip 15 can be attached to the rear (top) end of the sample container. This is also required when the hollow space is not completely but only, for instance, 90% filled with granules, in order to expedite the release of gases.

Another embodiment of the invention provides that a hollow space formed by the carrying tube 14 is filled with a granular material, which is bound with a binding agent made of an inorganic material. In this case, the cardboard tube 1, the coverplate 13 with the layer 12, and the spring clip 15 can be omitted.

It must be viewed as surprising that the problems which occur with the known devices, namely the danger that the two half dishes open as a result of the ferrostatic pressure when the melt flows into the sampling chamber, and a sufficient fixing of the sample container in the hollow space of the carrying tube can be solved by simply filling the hollow space of the carrying tube with granular material.

The hollow space filled with granular material that surrounds the sample container forms an adjustable buffer bulk, which leads to a slower and as a result more even flow of the melt, so that the formation of hollow spaces within the sample body is prevented. The formation of burrs resulting from steel leaving the sample container is also practically completely avoided in the area of the neck-shaped inlet orifice. Further, the granular material surrounding the sample container provides for an additional heat transfer by means of conduction. The inner thermal stress of the tube is extensively reduced and the release of gases is retarded.

The present invention may be embodied in other specific forms without departing from the spirit or essential attributes thereof and, accordingly, reference should be made to the appended claims, rather than to the foregoing specification as indicating the scope of the invention.

I claim:

1. A device for withdrawing samples from molten metals comprising a sample container formed from two metallic half dishes which fit together to form a shallow sampling chamber and arranged in the hollow space of a carrying tube, the sample container being provided with a neck-shaped inlet orifice for the molten metal and an externally projecting small quartz pipe which runs into said orifice, the improvement comprising the hollow space (10) surrounding the sample container (3) being substantially filled with granules (11) comprising a refractory material, the hollow space (10) being bordered on sides thereof by a cardboard tube (1) inserted into the carrying tube (14) and, on an end thereof opposite an inlet end thereof, by a layer (12) made of a porous, refractory material, over which a perforated cover plate (13) is arranged.

2. A device for withdrawing samples from molten metals comprising a sample container formed from two metallic half dishes which fit together to form a shallow sampling chamber and arranged in the hollow space of a carrying tube, the sample container being provided with a neck-shaped inlet orifice for the molten metal and an externally projecting small quartz pipe which runs into said orifice, the improvement comprising the small quartz pipe (5) projecting externally from a face of an immersion end of the device and being surrounded by a metal pipe (6) and the hollow space (10) surrounding the sample container (3) being substantially filled with granules (11) comprising a refractory material.

3. A device according to claim 2 wherein an immersion end of the metal pipe (6) is covered with a slag cap (8).

* * * * *